United States Patent [19]

Sherman

[11] Patent Number: 5,141,665

[45] Date of Patent: Aug. 25, 1992

[54] CLEANING, CONDITIONING, STORING AND WETTING SYSTEM AND METHOD FOR RIGID GAS PERMEABLE CONTACT LENSES AND OTHER CONTACT LENSES

[75] Inventor: Guy J. Sherman, St. Tammany, La.

[73] Assignee: Sherman Laboratories, Inc., Mandeville, La.

[21] Appl. No.: 551,514

[22] Filed: Jul. 11, 1990

Related U.S. Application Data

[63] Continuation of Ser. No. 242,410, Sep. 8, 1988, abandoned, which is a continuation-in-part of Ser. No. 140,075, Dec. 31, 1987, abandoned, which is a continuation-in-part of Ser. No. 32,891, Mar. 31, 1987, abandoned.

[51] Int. Cl.$^5$ .......................... C11D 1/68; C11D 3/48; A61K 9/08
[52] U.S. Cl. ................................... 252/106; 252/89.1; 514/839; 514/840
[58] Field of Search ............... 252/106, 89.1; 514/839, 514/840

[56] References Cited

U.S. PATENT DOCUMENTS 4,543,200 9/1985 Sherman ........................... 252/106
4,560,491 12/1985 Sherman ........................... 252/106

OTHER PUBLICATIONS

Coles, W. H. "Effects of Antibiotics On the In Vitro Rabbit Endothelium" 1975.
Grant, W. M. *Toxicology of the Eye*, pp. 143–144.

*Primary Examiner*—Paul Lieberman
*Assistant Examiner*—Kery A. Fries
*Attorney, Agent, or Firm*—Jenner & Block

[57] ABSTRACT

A system and method for cleaning, conditioning, storing and wetting rigid gas permeable contact lenses is provided. The system includes a cleaning, conditioning and storing solution and a separate wetting solution. Both solutions contain hydrophilic disinfectants or preservatives which do not inhibit proper wetting of rigid gas permeable contact lenses. The lenses are stored in the cleaning, conditioning and storing solution during nonwearing periods. This storage also acts as a secondary or backup cleaning treatment to help remove any residual contaminants after the primary cleaning with this solution.

In accordance with another embodiment of the invention, a preservative system is provided for a contact lens solution that comprises high purity benzyl alcohol.

59 Claims, No Drawings

CLEANING, CONDITIONING, STORING AND WETTING SYSTEM AND METHOD FOR RIGID GAS PERMEABLE CONTACT LENSES AND OTHER CONTACT LENSES

RELATED APPLICATION

This is a continuation of application Ser. No. 07/242,410 filed Sep. 8, 1988 abandoned, which is a continuation-in-part of U.S. application Ser. No. 140,075, filed Dec. 31, 1987, abandoned, which is a continuation-in-part of U.S. application Ser. No. 032,891, filed Mar. 31, 1987 (abandoned).

FIELD OF THE INVENTION

The present invention relates to a preservative system for contact lens solutions and to a rigid gas permeable contact lens cleaning, storing, conditioning and wetting system and method. More particularly, the present invention relates to a cleaning, storing, conditioning and wetting system and method for rigid gas permeable contact lenses that allows effective cleaning and conditioning and proper wetting of rigid gas permeable lenses.

BACKGROUND OF THE INVENTION

Rigid gas permeable (RGP) lenses are manufactured from materials that exhibit a high degree of polarity, resulting in a strong interaction with proteins and other tear constituents that ultimately produce tenacious surface deposits. Current state of the art care systems combat this problem through the use of unpreserved abrasive cleaners that produce microscopic scratches which, in time, shorten the useful life of the lens. Some attempts have been made to competitively block surface deposition by so-called "conditioning" solutions, but this approach involves the use of cytotoxic preservatives and does not eliminate the need for the abrasive cleaner.

Proteolytic enzymes have been of marginal value in controlling surface deposition because their action is limited to proteinaceous material. Multifunctional esterases capable of lysing both proteins and lipids failed to significantly improve on the results obtained with their proteolytic counterparts and the consequences of their usage was a delayed, but persistent, surface deposition and premature loss of the lens.

Aside from the problem of ultimate surface contamination, the RGP lens wearer is also faced with an initial discomfort problem until the lens completely hydrates, at which time it displays its best wetting and consequently its greatest comfort. In order to ensure that this maximal comfort is maintained, it is essential that the wettability of the surface be maintained. Moreover, the capability of the lens to resist surface deposition is also directly related to the maintenance of its wettability. The current state of the art lens care systems do not maintain optimal wettability over long periods of time because they are passive systems formulated to deal with the result of the polymer's surface interactions rather than to eliminate its cause.

RGP lenses have the potential of providing an unsurpassed level of comfort for a rigid lens. Unfortunately, the wearer realizes this benefit for only a short period of time because the current passive RGP care systems are unable to maintain this property.

Initial treatment of new RGP lenses usually includes cleaning with an abrasive cleaner, after which the lens may be soaked in a viscous, polar solution, to purportedly interact with active sites on the lens surface and thereby block their interaction with contaminants. The failure of this system to achieve this result is evident in the fact that the abrasive cleaner must be used on a daily basis and even then, adjunctive products are frequently needed. "Conditioning" then must require abrading the surface as part of the process. Aside from the lack of efficacy of this system, it shortens the functional life of the lens thereby producing a financial loss for the wearer.

Known and/or FDA approved cleaning and wetting solutions for RGP contact lenses utilize hydrophobic preservatives or disinfecting agents such as benzalkonium chloride or chlorhexidine. These hydrophobic materials tend to reduce the wettability of RGP lenses, especially fluorinated RGP lenses, thereby making cleaning and wetting more difficult. A surfactant polymer may be added to such formulations specifically to attempt to overcome the effect of the hydrophobic preservative.

A need exists for an active RGP lens care system that deals with the causes of surface deposition and poor wetting without resorting to the use of abrasives, cytotoxic chemicals or enzymes, and without the use of preservatives that reduce the wettability of the lenses.

A need also exists for a new preservative system for contact lens solutions.

SUMMARY OF THE INVENTION

In accordance with the present invention, a preservative system and a solution system and method for cleaning, conditioning and wetting rigid gas permeable (RGP) contact lenses and other contact lenses is provided. Rigid gas permeable or RGP contact lenses feel rigid, similar to hard contact lenses, but have substantial gas permeability. RGP contact lenses are made or can be made from a number of materials. RGP lenses can be made from silicone acrylate (which may be fluorinated), silicone, styrene, fluorinated materials, urethane and similar materials. The fluorinated silicone acrylate material usually has greater oxygen permeability, which is beneficial to the wearer, but is more difficult to clean and wet. The system and method of the present invention is particularly suited for care of fluorinated silicone acrylate RGP contact lenses.

Preservatives or disinfectants used in prior RGP cleaning and wetting solutions, such as benzalkonium chloride and chlorhexidine, are electropositive, hydrophobic compounds. These compounds exhibit an affinity for the surface of RGP contact lenses, the material of which is electronegative. As a result, benzalkonium chloride or chlorhexidine becomes bound to the RGP lens surface. As a result, these preservatives, which are also hydrophobic, reduce the wettability of the RGP lens. In contrast, the preservatives or disinfectants in accordance with the present invention are electronegative and hydrophilic and do not deleteriously bind to the RGP lens.

The cleaning, conditioning and wetting solution system of the present invention includes a sterile aqueous cleaning, storing and conditioning solution and a separate, sterile aqueous wetting solution that is compatible with the cleaning and conditioning solution. The wetting solution can also be used as an in-eye lubricant. Preferably, the system should be obtained and used in kit form to ensure proper care of a person's RGP contact lenses. Both solutions, which are formulated for and are compatible with RGP lenses, avoid the use of a hydrophobic preservative or disinfectant, such as benzalkonium chloride or chlorhexidine, which have been found to reduce the wettability of an RGP contact lens. This is especially the case with fluorinated RGP contact lenses. The need for an additional surfactant to attempt to overcome the hydrophobic properties of the preservative or disinfectant is eliminated. The need for a daily abrasive cleaner is also avoided.

The cleaning and conditioning components of the cleaning, conditioning and storing solution are specifically chosen to clean and condition RGP lenses, as well as be suitable for storage of RGP lenses. This solution allows RGP lenses to be conditioned without abrading or damaging the surface of the lens and allows the lens to maintain its wettability and deposit resistance throughout the wearing period and without the need for adjunctive solutions, such as enzyme cleaners and in-eye lubricants, for example.

The cleaning, conditioning and storage solution is a nonabrasive sterile aqueous solution that includes a hydrophilic disinfectant compound or compounds and a suitable component for cleaning and conditioning RGP contact lenses.

By hydrophilic disinfectant is meant that the disinfectant or preservative or combination of disinfectants or preservatives are hydrophilic. Preferably, none of the disinfectant compounds present in the solution are hydrophobic.

The disinfectant or preservative for the cleaning, conditioning and storing solution and for the wetting solution in accordance with the invention comprises two compounds, benzyl alcohol and a water soluble salt of ethylenediaminetetraacetic acid (EDTA or edetate), which is an adjuvant disinfectant, preferably the trisodium salt of EDTA. No other disinfectants are necessary. The disinfectant compounds are present in amounts effective to maintain the sterility of the composition. Usually, these amounts are about 0.05% to about 1.0% (preferably about 0.1%) benzyl alcohol, and, for the cleaning solution, about 0.025% to about 0.75% (preferably about 0.5%) of the salt of EDTA (from about 0.025% to about 0.25 and preferably about 0.1 for the wetting solution), by weight of the total solution (whether a cleaning, wetting, conditioning or other solution), including water, will be effective for preserving the solution. Alternatively, the cleaning solution and wetting solution disinfectant may comprise sorbic acid (usually about 0.001 to about 0.35% and preferably 0.1), a water soluble salt of EDTA (in an amount as previously described) and optionally boric acid (usually up to about 1.0% and preferably 0.6%). Boric acid is incompatible with polyvinyl alcohol (PVA) and thus should not be used in a wetting solution that contains PVA.

The benzyl alcohol used in accordance with the present invention should be a high purity benzyl alcohol. It has been discovered that standard grades of benzyl alcohol available for pharmaceutical use contain significant amounts of benzaldehyde. Benzaldehyde is an impurity present in commercially available benzyl alcohol. While benzaldehyde does not appear to compromise the bactericidal activity of benzyl alcohol, it has been discovered that benzaldehyde, when present in contact lens solutions in sufficient concentration, acts as an eye irritant. Benzyl alcohol at high enough concentrations (about 2% by weight or more) can also act as an ocular irritant and such benzyl alcohol concentrations should be avoided.

The benzyl alcohol that is incorporated in the contact lens solutions of the present invention should be free of a benzaldehyde concentration such that when incorporated into a contact lens solution, an excessive benzaldehyde concentration would result, and is sometimes referred to herein as "high purity benzyl alcohol." As used herein "excessive benzaldehyde concentration" means that concentration of benzaldehyde which causes significant eye irritation. Usually, in accordance with the invention, the concentration of benzaldehyde in the final contact lens solution should be no more than about one ppm (by weight of the total solution) and preferably under about one ppm by weight of the total solution, and most preferably about 0.1 ppm or less by weight of the total solution.

Suitable benzyl alcohol (high purity benzyl alcohol) for use in accordance with the invention can be obtained from Akzo Chemic America of Edison, N.J. and Stauffer Chemical Company of Westport, Conn., a subsidiary of Chesebrough Ponds Inc. Akzo Chemic can provide, for example, benzyl alcohol containing less than about 100 ppm benzaldehyde by weight benzyl alcohol. Methods of removing benzaldehyde from benzyl alcohol are well known to those skilled in the art. Typically, "high purity benzyl alcohol," as used in accordance with the invention will be benzyl alcohol suitable for pharmaceutical use and having a benzaldehyde concentration of less than or equal to about 100 ppm by weight of the benzyl alcohol.

An antioxidant material can be present in the composition to prevent or minimize oxidation of the benzyl alcohol. Suitable antioxidants that can be used include sodium bisulfite and various forms of Vitamin A, such as esters of Vitamin A, preferably Vitamin A palmitate, which has a biopotency of about $1.7 \times 10^6$ I.U./gram.

In accordance with another aspect of the invention, the disinfectant consists of, or consists essentially of, two compounds. This two component combination can be benzyl alcohol and a water soluble salt of EDTA, or sorbic acid and a water soluble salt of EDTA in amounts as previously specified. Thus, disinfectant materials such as chlorhexidine, benzalkonium chloride, thimerosal or trimethoprim, or some other disinfectant, are not needed or used in accordance with the invention. Moreover, materials such as trimethoprim have low solubility in water and thus are hydrophobic. Such materials normally would not be contemplated for use in accordance with the invention.

The cleaning and conditioning component may comprise an alkylarylpolyether alcohol non-ionic detergent and an amphoteric surface active agent in effective amounts for cleaning and conditioning an RGP contact lens. This combination of materials has been found effective to clean and condition RGP contact lenses. By "condition" is meant that the RGP lens surface is cleaned and that surface interactions which inhibit wetting (such as a surface charge) are eliminated or neutralized. The cleaning and conditioning component is compatible with RGP lenses so as to allow storage of the lenses in the cleaning, conditioning and storage solution. Usually, about 0.5% to about 10% of the amphoteric surface active agent and from about 0.005% to about 5.0% of the alkylarylpolyether alcohol, by weight of the total cleaning, conditioning and storing solution, including water, will be effective for providing the desired cleaning and conditioning of RGP lenses, and will permit storage of the lenses in the solution. Other types of cleaning components may be suitable for use in accordance with the invention, as long as the desired cleaning and conditioning of RGP contact lenses is provided.

In accordance with another aspect of the invention, the cleaning, storing and conditioning solution consists of, or consists essentially of: (a) a hydrophilic preservative consisting of (i) benzyl alcohol and a water soluble salt of EDTA or (ii) sorbic acid and a water soluble salt of EDTA; (b) at least one cleaning and conditioning component; and (c) sterile water. Various additional components may also be included as specified in the following Description of The Preferred Embodiments and as recited in Tables 1 and 2.

The wetting solution of the present invention is a sterile aqueous solution that includes a hydrophilic preservative or disinfectant and at least one wetting agent selected from polyvinylalcohol (PVA) and polyvinylpyrrolidone (PVP).

The hydrophilic preservative can be as previously described and may also include sorbic acid as an adjuvant bactericide, usually in the range of from about 0.001% to about 0.20% by weight of the total composition.

In accordance with another aspect of the invention the wetting solution may consist of or consist essentially of: (a) a hydrophilic preservative consisting of, or consisting essentially of, (i) benzyl alcohol and a water soluble salt of EDTA; or (ii) sorbic acid and a water soluble salt of EDTA; (b) at least one wetting agent selected from PVA and PVP; and (c) sterile water. Various additional components may also be present as recited in the following Description of The Preferred Embodiments and as recited in Tables 3 and 4.

Preferably, the wetting solution has a tonicity of from about 0.91 to about 1.65 and a pH in the range of from about 6.5 to 8.5. Various salts and buffers can be included to provide the desired tonicity and pH.

In accordance with a broader aspect of the invention, a new preservative system is provided that can be used for numerous types of contact lens solutions, including solutions for hard, soft and gas permeable contact lenses. The preservative system comprises high purity benzyl alcohol in an amount sufficient to preserve the sterility of the solution. Usually, the benzyl alcohol will be present in an amount of from about 0.05% to about 1.0% by weight of the total composition. The high purity benzyl alcohol used in accordance with the invention can be used as a preservative for a wide variety of contact lens solutions, including, for example, wetting, rinsing, soaking and cleaning solutions, in-eye wetting and rewetting solutions, and sterilizing and storage solutions, which can be saline solutions.

Contact lens solutions in accordance with the present invention have been approved by the United States Food and Drug Administration.

DESCRIPTION OF THE PREFERRED EMBODIMENTS

RGP lenses destined for the solution system and method of the present invention should preferably be cleaned with the cleaning, conditioning and storing solution as follows. The lens is placed in the palm of the hand and then covered with the solution. The lens is then bathed and patted with the index finger of the other hand. The lens should not be rubbed, for example, such as between the thumb and forefinger, since this may warp or scratch the lens.

After cleaning, between wearing periods, the lenses should be thoroughly rinsed with tap water and then stored in the cleaning, conditioning and storing solution. Usually, regardless of the wearer's cleaning technique and type of cleaning solution, some residual contaminants will remain on the lens. Because the cleaning solution of the present invention is also the storage solution, and because of its formulation, at least a portion of, if not all, residual contaminants are removed or loosened during storage. This is contrary to the prior art, which does not contemplate utilizing a cleaning solution for storage. Such a system is especially advantageous since the wearer may often fail to clean the lens properly or sufficiently, or may even forget to clean the lens at all, prior to storage. Thus, storage of the lens in the cleaning, storing and conditioning solution acts as a secondary or backup cleaning treatment, in addition to storing and otherwise conditioning the lens. When one desires to wear the lenses, they should be rinsed with tap water or fresh saline, wetted with the wetting solution of the present invention and inserted into the wearer's eye.

An especially preferred cleaning, conditioning and storage solution in accordance with the invention and especially suitable for RGP contact lenses has the composition:

TABLE 1

| Component | Amount (% by weight) |
| --- | --- |
| Amphoteric surface active agent (Miranol 2 MCA Modified) | 8.0 |
| alkylarylpolyether alcohol (Triton X-100) | 2.33 |
| high purity benzyl alcohol (less than 100 ppm benzaldehyde) | 0.1 |
| trisodium edetate | 0.5 |
| propylene glycol | 2.0 |
| purified water | to 100 |

One preferred type of amphoteric surface active agent is 2-cocoyl-2-imidazolinium lauryl sulfate-1 carboxymethyloxyethyl-1-carboxymethyl disodium which is also sold under the trade name "Miranol 2 MCA Modified" by the Miranol Chemical Company, Inc. of Irvington, N.J. The amphoteric surface active agent is present in the preferred composition of the present invention in an amount of from about 0.5% to about 20% of the total weight of the aqueous composition and preferably comprises about.8.0% of the total aqueous composition. One substitute for "Miranol 2 MCA Modified" is "Miranol MHT" which is also sold by the Miranol Chemical Company, Inc.

The preferred type of alkylarylpolyether alcohol in the cleaning, conditioning and storing composition of the present invention is isooctylphenoxypolyethoxyethanol. The most preferred type of isooctylphenoxypolyethoxyethanol contains about 9 units of ethoxyethanol per unit of isooctylphenol and has a molecular weight of about 630. The most preferred alkylarylpolyether alcohol is sold under the trademark "Triton X-100" by the Rohm & Haas Company of Philadelphia, Pa. The alkylarylpolyether alcohol is present in a concentration of from about 0.005% to about 5.0%, and preferably about 2.33%, by weight of the total aqueous composition. The alkylarylpolyether alcohols are also known as octylphenolethyleneoxide. The alkylarylpolyether alcohol complements the cleansing characteristics of the block copolymers and helps to remove ocular secretions, proteinaceous deposits and other materials which may be deposited upon the surfaces of the lens.

Preferably, propylene glycol is present in the cleaning compositions in accordance with the invention in an amount of from about 0.005% to about 5.0% by weight of the total aqueous composition. Propylene glycol helps provide for ease of rinsing the cleaning composition from the contact lens surface and also acts as a preservative of the composition and a thickening agent.

The cleaning, conditioning and storing solution in accordance with the invention generally has a pH of from about 5.0 to about 6.5. This slightly acidic pH helps to dissolve protein and aids in rinsing the composition from the lens.

Another example of a cleaning, conditioning and storing composition in accordance with the invention which is particularly suitable for RGP contact lenses is:

TABLE 2

| Component | Amount (% by weight) |
| --- | --- |
| Miranol 2 MCA Modified | 8.0 |
| propylene glycol | 0.67 |
| Triton X-100 | 2.33 |
| trisodium edetate | 0.5 |
| sorbic acid | 0.1 |
| sodium bisulfite | 0.05 |
| sterile water | to 100 |

An especially preferred wetting solution in accordance with the present invention which is especially suitable for RGP lenses has the composition:

TABLE 3

| Component | Amount (% by weight) |
| --- | --- |
| polyvinylalcohol | 1.0 |
| polyvinylpyrrolidone (Plasdone ® C) | 0.5 |
| high purity benzyl alcohol (less than 100 ppm benzaldehyde) | 0.1 |
| trisodium edetate | 0.1 |
| sorbic acid | 0.05 |
| hydroxyethylcellulose | 0.35 |
| sodium bisulfite | 0.02 |
| sodium carbonate | 0.1375 |
| sodium phosphate | 0.005 |
| sodium biphosphate | 0.005 |
| sodium chloride | 0.748 |
| potassium chloride | 0.280 |
| sterile water | to 100 |

The high purity benzyl alcohol listed in Table 3 was obtained from Akzo Chemic and had a benzaldehyde concentration of 82 ppm.

Another cleaning composition in accordance with the invention, which is especially useful for cleaning soft contact lenses has the formula:

TABLE 4

| Component | Amount (% by weight) |
| --- | --- |
| Miranol 2 MCA | 3.0 |
| Pluronic F108 | 6.0 |
| Triton X-100 | 0.5 |
| Propylene Glycol | 1.0 |
| High Purity Benzyl Alcohol (less than 100 ppm benzaldehyde) | 0.1 |
| trisodium edetate | 0.5 |
| potassium chloride | 0.3 |
| sodium chloride | 0.616 |
| sodium bicarbonate | 0.05 |
| Balance USP purified water | |

An especially suitable wetting and in-eye comfort drop for soft and RGP contact lenses and lens wearers has the formula:

TABLE 5

| Component | Amount (% by weight) |
| --- | --- |
| high purity benzyl alcohol (less than 100 ppm benzaldehyde) | 0.1 |
| Polysorbate 80 (Vitamin A emulsifier) | 0.1 |
| Vitamin A Palmitate (1.7 × 10$^6$ I.V./gram) | 0.0196 |
| polyvinyl pyrrolidone | 0.5 |
| polyvinyl alcohol | 1.0 |
| hydroxyethylcellulose | 0.27 |
| trisodium EDTA | 0.1 |
| potassium chloride | 0.28 |
| sodium chloride | 0.6 |
| sodium biphosphate | 0.005 |
| sodium phosphate | 0.005 |
| sodium carbonate | 0.02 |

An especially suitable wetting and in-eye comfort drop for RGP lenses (such as silicone acrylate and fluorosilicone acrylate RGP lenses) and lens wearers has the formula:

TABLE 6

| Component | Amount (% by weight) |
| --- | --- |
| high purity benzyl alcohol (less than 100 ppm benzaldehyde) | 0.1 |
| sorbic acid | 0.05 |
| sodium bisulfite | 0.02 |
| polyvinylpyrrolidone | 0.5 |
| polyvinylalcohol | 1.0 |
| hydroxyethylcellulose | 0.33 |
| trisodium edetate | 0.1 |
| potassium chloride | 0.280 |
| sodium chloride | 0.6 |
| sodium biphosphate | 0.005 |
| sodium phosphate | 0.005 |
| sodium carbonate | 0.06 |

The wetting solution includes at least one component suitable for wetting contact lenses. The wetting system can include a viscosity-building agent and a wetting agent suitable for RGP contact lenses. Suitable viscosity-building agents include water soluble cellulosic polymers, which may be synthetic or natural, for example. Such materials also assist in wetting the lenses. Suitable wetting agents include polyvinyl alcohol and polyvinylpyrrolidone and mixtures thereof, for example. Other suitable viscosity-building agents and wetting agents for RGP contact lens wetting solutions can be used.

Suitable cellulosic polymers include hydroxyethylcellulose, methylcellulose, carboxymethylcellulose, natural gums and mixtures thereof. Usually, the amount of cellulosic polymer present in the composition is from about 0.05% to about 0.80% by weight of the total composition.

Usually, the wetting composition will have a viscosity of about 20 to 40 cps at 25° C. Medium grade cellulosic polymers are useful for achieving the desired viscosity.

In the especially preferred composition of Table 3, sorbic acid functions as a preservative and, when present, will usually be in the range of from about 0.001% to about 0.35%, preferably about 0.05%.

Preferably, the polyvinyl alcohol utilized is fully hydrolized. Generally, the amount of polyvinyl alcohol present in the composition is from about 0.5% to about 2.5% by weight of the total composition.

Preferably, an additional wetting compound, a polyvinylpyrrolidone polymer, will be utilized, usually in an amount of from about 0.5% to about 2.0% by weight of the total composition.

It is to be understood that the invention is not limited to the foregoing types of wetting agents and viscosity-building agents. Any type of material which can be used to provide the desired wetting action for RGP contact lenses, or other contact lenses, and which is compatible with the preservative system of the present invention and is otherwise suitable for use in a wetting solution or an RGP or other contact lens wetting solution can be utilized.

An especially preferred wetting system contains hydroxyethylcellulose, polyvinylpyrrolidone and polyvinyl alcohol. A preferred hydroxyethylcellulose is available from Hercules, Inc. of Wilmington, Del. under the trade designation "250 H." A preferred polyvinylpyrrolidone is available from GAF Corporation of New York, N.Y. under the name Plasdone ® C. A preferred polyvinyl alcohol is available from the Monsanto Company of St. Louis, Mo. under the name of "Galvatol" which is partially hydrolized.

The wetting compositions of the present invention are preferably buffered and slightly acid or neutral. The preferred pH range is from about 6.5 to about 8.5. Suitable buffers are known in the art. Especially suitable buffers include sodium bicarbonate and tribasic sodium phosphate ($Na_3PO_4.12H_2O$). The preferred combination of buffers is bicarbonate, tribasic sodium phosphate and sodium biphosphate ($NaH_2PO_4$).$H_2O$, in amounts to provide and maintain the desired pH. The remainder of the wetting composition is sterile water U.S.P. and preferably includes combinations of essentially neutral and alkaline salts compatible with ocular tissue and RGP contact lens materials, generally present in a concentration to provide an aqueous composition salt content equivalent to from about 0.91 to about 1.65 tonicity. Sodium chloride can be present in the RGP contact lens wetting composition in an amount from about 0.05% to about 2.0% by weight of the total aqueous composition, for example, and preferably in an amount of about 0.75% by weight of the total aqueous composition. Potassium chloride is another salt which is preferably used in conjunction with sodium chloride and should generally be present in an amount of from about 0.05% to about 2.0% by weight of the total aqueous composition and preferably in an amount of about 0.28% by weight of the total aqueous composition.

Another wetting composition for RGP contact lenses in accordance with the invention is:

TABLE 7

| Component | Amount (% by weight) |
| --- | --- |
| polyvinylpyrrolidone (Plasdone ® C) | 2.0 |
| sorbic acid | 0.1 |
| boric acid | 0.6 |
| trisodium EDTA | 0.1 |
| hydroxyethyl cellulose | 0.32 |
| sodium bisulfite | 0.02 |
| sodium carbonate | 0.14 |
| sodium phosphate | 0.005 |
| sodium biphosphate | 0.005 |
| sodium chloride | 0.75 |
| potassium chloride | 0.28 |
| sterile water | to 100 |

A daily cold disinfecting solution for soft contact lenses in accordance with the invention has the formula:

TABLE 8

| Component | Amount (% by weight) |
| --- | --- |
| high purity benzyl alcohol (less than 100 ppm benzaldehyde) | 1.0 |
| Miranol M5-1 | 1.0 |
| boric acid | 0.12 |
| sodium borate | 0.12 |
| trisodium edetate | 0.15 |
| sodium chloride | 0.3 |
| sodium biphosphate | 0.01 |
| sodium phosphate | 0.01 |

The cold disinfecting solution can be used, for example, by cleaning and then storing the soft lenses in the solution between nonwearing periods, such as overnight.

EXAMPLE 1

A study was conducted to evaluate the preservative efficacy with rechallenge of contact lens solutions in accordance with the invention according to *United States Pharmacopeia* (USP) Twenty-First Revision and the Draft Testing Guidelines for Class III Contact Lens Solutions, July 1985 Revision.

The test system consisted of:
*Staphylococcus aureus*, ATCC 6538
*Pseudomonas aeruginosa*, ATCC 9027
*Candida albicans*, ATCC 10231
*Aspergillus niger*, ATCC 16404
*Escherichia coli*, ATCC 8739
from STS Rept. M 88-778.

The challenge organisms were prepared as follows.

*E. coli, P. aeruginosa* and *S. aureus* were inoculated onto Tryptic Soy Agar (TSA) slants and incubated for 18-24 hours at 32°-35° C., transferred onto fresh TSA slants and reincubated for 18-24 hours at 32°-35° C. The cultures were harvested with 0.067M phosphate buffer and washed using the following procedure:

a) Centrifuged at 5,000 rpm at 5° C. for 10 minutes.
b) Supernatant decanted.
c) The pellet resuspended with fresh phosphate buffer.
d) a-c was repeated once.

*C. albicans* was grown on Sabouraud Dextrose Agar (SDA) slants at 20°-25° C. for 24-48 hours and prepared in the manner as the bacteria.

*A. niger* was grown on Tryptic Soy Agar Sabouraud Dextrose Agar (SDA) slants for 5-7 days at 20°-25° C. The spores were harvested using phosphate buffer with 0.1% Tween 80. The spores were washed in the same manner as the bacteria.

The concentration of all challenge organisms was adjusted spectrophotometrically with phosphate buffer to approximately $2 \times 10^8$ organisms/ml.

For each challenge organism, the following solutions were aseptically dispensed into sterile tubes: Test solution 20 ml of a contact lens solution having the formula set forth in Table 5 and a positive control 20 ml 0.1% peptone.

These tubes were inoculated with 0.1 ml of the appropriate inoculum suspension (approximately $1 \times 10^6$ organisms/ml) and mixed thoroughly. The final concentration was between $10^5$ and $10^6$ cfu/ml.

Within 15 minutes after the addition of the inoculum suspension and at 7, 14, 21 and 28 days exposure a 1.0 ml aliquot was aseptically removed from each tube and added to 9.0 ml sterile Dey Engley Broth (DEB) ($10^{-1}$ dilution). These samples were serially diluted in DEB to $10^{-3}$ (1 ml into 9 ml DEB twice sequentially). 0.1 ml and 1.0 ml aliquots from the $10^{-1}$ and $10^{-3}$ dilutions were plated using the pour plate method with Dey Engley Broth (DEB).

Due to growth in the positive control solution at later exposure times, dilutions were carried out to a final concentration of $10^{-7}$. Plates were incubated at 30°–35° C. for 48–72 hours. Following incubation, plate counts were recorded and challenge organism reduction was determined. Test and control solutions were stored at 20°–25° C. for the duration of the 28 day test.

The rechallenge evaluation was conducted as follows.

Fresh inoculum suspensions of the challenge organisms were prepared as in 1.0 and 2.0.

1:9 dilutions of 4.1 were prepared with phosphate buffer to an approximate concentration of $2.0 \times 10^7$ organisms/ml.

Immediately following the fourteen (14) day plating, all samples except the positive control were rechallenged with 0.1 ml of the appropriate challenge organism.

An additional positive control was prepared to verify the concentration and monitor the growth of the rechallenge inoculum for the remainder of the twenty-eight (28) day test period.

Within fifteen (15) minutes of the addition of the rechallenge and at twenty-one (21) and twenty-eight (28) days exposure, samples were taken, diluted and plated as in 3.3.

A neutralizer efficacy screen was completed for each exposure time and consisted of a one ml of uninoculated test solution was aseptically added to a 9.0 ml DEB blank and thoroughly mixed. Duplicate 1 ml aliquots from the Broth were transferred to petri plates and one ml of a *Bacillus subtilis* spore suspension (containing approximately 100 cells/ml) was added. All plates were poured using Dey Engley Agar. The plates were incubated at 32°–35° C. for 48–72 hours.

The results of this study are presented as follows.

Tables 9–13 each table showing the CFU (Colony forming units) of organism in the test solution and positive controls at each time point. Neutralizer Efficacy results found in Table 14.

The concentrations of *S. aureus, P. aeruginosa* and *E. coli* were reduced to at least 0.1% (three log values) of the initial concentration within the first fourteen (14) days. The concentration of viable *C. albicans* and *A. niger* remained at or below the initial concentration during the first fourteen (14) days.

After rechallenge, the concentrations of *S. aureus, P. aeruginosa, C. albicans* and *A. niger* remained within the specifications for preservative efficacy with rechallenge.

*E. coli* was mistakenly rechallenged at a concentration of approximately $10^6$ which is one log higher than the specified level. This additional organic load resulted in a reduction of slightly less than 3 log values. It is believed a $10^5$ challenge would have resulted in a full 3 log reduction value. The belief that *E. coli* would have been reduced by 3 logs is further supported by the fact that in this test *P. aeruginosa* was reduced by at least 4 logs.

The concentration of the positive controls were not reduced more than 90.0% (one log value).

There was no significant reduction of *B. subtilis* during the Neutralizer Efficacy Screen.

The contact lens solution in accordance with the invention and as tested with *S. aureus, P. aeruginosa, C. albicans* and *A. niger* meet the requirements of Preservative Efficacy with rechallenge. *E. coli* was overchallenged by 90% of the 14 day rechallenge time; however, reduction of this organism was approximately 3 log values.

TABLE 9

| Time Interval | System Evaluated | Dilution | S. aureus A Plate Count | B Plate Count | Average A&B CFU/ml |
|---|---|---|---|---|---|
| T = 0 day | Test | $10^4$ | 71 | 78 | $7.5 \times 10^5$ |
| | PC* | $10^5$ | 40 | 43 | $4.2 \times 10^6$ |
| T = 7 day | Test | $10^1$ | 0 | 0 | less than 10 |
| | PC | $10^6$ | 146 | 62 | $1.0 \times 10^8$ |
| T = 14 day | Test | $10^1$ | 0 | 0 | less than 10 |
| | PC | $10^6$ | 106 | 140 | $1.2 \times 10^8$ |
| T = 14 day Rechallenge | Test | $10^3$ | 255 | 265 | $2.6 \times 10^5$ |
| | PCR** | $10^3$ | 260 | 238 | $2.5 \times 10^5$ |
| T = 21 day | Test | $10^1$ | 0 | 0 | less than 10 |
| | PC | $10^7$ | 86 | 47 | $6.7 \times 10^8$ |
| | PCR | $10^6$ | 142 | 159 | $1.5 \times 10^8$ |
| T = 28 day | Test | $10^1$ | 0 | 0 | less than 10 |
| | PC | $10^6$ | 55 | 17 | $3.6 \times 10^7$ |
| | PCR | $10^6$ | 72 | 77 | $7.4 \times 10^7$ |

*Positive Control
**Rechallenge Positive Control

TABLE 10

| Time Interval | System Evaluated | Dilution | P. aeruginosa A Plate Count | B Plate Count | Average A&B CFU/ml |
|---|---|---|---|---|---|
| T = 0 day | Test | $10^4$ | 43 | 84 | $6.4 \times 10^5$ |
| | PC* | $10^4$ | 116 | 178 | $1.5 \times 10^6$ |
| T = 7 day | Test | $10^1$ | 0 | 0 | less than 10 |
| | PC | $10^5$ | approx 1000 | approx 1400 | $1.2 \times 10^8$ |
| T = 14 day | Test | $10^1$ | 0 | 0 | less than 10 |
| | PC | $10^7$ | 50 | 30 | $4.0 \times 10^8$ |
| T = 14 day | Test | $10^3$ | 284 | 219 | $2.5 \times 10^5$ |

TABLE 10-continued

P. aeruginosa

| Time Interval | System Evaluated | Dilution | A Plate Count | B Plate Count | Average A&B CFU/ml |
|---|---|---|---|---|---|
| Rechallenge | PCR | $10^3$ | 138 | 163 | $1.5 \times 10^5$ |
| T = 21 day | Test | $10^1$ | 50 | 47 | $4.9 \times 10^2$ |
| | PC | $10^7$ | 168 | 155 | $1.6 \times 10^9$ |
| | PCR | $10^7$ | 63 | 65 | $6.4 \times 10^8$ |
| T = 28 day | Test | $10^1$ | 0 | 0 | less than 10 |
| | PC | $10^7$ | 74 | 65 | $7.0 \times 10^8$ |
| | PCR | $10^7$ | 32 | 35 | $3.4 \times 10^8$ |

TABLE 11

E. coli

| Time Interval | System Evaluated | Dilution | A Plate Count | B Plate Count | Average A&B CFU/ml |
|---|---|---|---|---|---|
| T = 0 day | Test | $10^4$ | 95 | 126 | $1.1 \times 10^6$ |
| | PC | $10^4$ | 182 | 176 | $1.8 \times 10^6$ |
| T = 7 day | Test | $10^3$ | 51 | 67 | $5.9 \times 10^4$ |
| | PC | $10^7$ | 42 | 31 | $3.6 \times 10^8$ |
| T = 14 day | Test | $10^1$ | 1 | 1 | $1.0 \times 10^1$ |
| | PC | $10^7$ | 37 | 46 | $4.2 \times 10^8$ |
| T = 14 day Rechallenge | Test | $10^4$ | 52 | 44 | $4.8 \times 10^5$ |
| | PCR | $10^5$ | 7 | 15 | $1.1 \times 10^6$ |
| T = 21 day | Test | $10^3$ | 115 | 162 | $1.4 \times 10^5$ |
| | PC | $10^6$ | 164 | 150 | $1.6 \times 10^8$ |
| | PCR | $10^6$ | 77 | 63 | $7.0 \times 10^7$ |
| T = 28 day | Test | $10^2$ | 52 | 21 | $3.7 \times 10^3$ |
| | PC | $10^7$ | 61 | 55 | $5.8 \times 10^8$ |
| | PCR | $10^6$ | 315 | 301 | $3.1 \times 10^8$ |

TABLE 12

C. albicans

| Time Interval | System Evaluated | Dilution | A Plate Count | B Plate Count | Average A&B CFU/ml |
|---|---|---|---|---|---|
| T = 0 day | Test | $10^4$ | 72 | 70 | $7.1 \times 10^5$ |
| | PC | $10^4$ | 119 | 100 | $1.1 \times 10^6$ |
| T = 7 day | Test | $10^4$ | 142 | 150 | $1.5 \times 10^6$ |
| | PC | $10^7$ | 66 | 77 | $7.2 \times 10^8$ |
| T = 14 day | Test | $10^3$ | 102 | 108 | $1.1 \times 10^5$ |
| | PC | $10^6$ | 98 | 96 | $9.7 \times 10^7$ |
| T = 14 day Rechallenge | Test | $10^4$ | 24 | 37 | $3.1 \times 10^5$ |
| | PCR | $10^3$ | 102 | 109 | $1.1 \times 10^5$ |
| T = 21 day | Test | | | | |
| | PC | $10^5$ | 90 | 87 | $8.9 \times 10^6$ |
| | PCR | $10^7$ | 55 | 65 | $6 \times 10^8$ |
| T = 28 day | Test | $10^3$ | 62 | 96 | $7.9 \times 10^4$ |
| | PC | $10^5$ | 110 | 83 | $9.7 \times 10^6$ |
| | PCR | $10^6$ | 270 | 212 | $2.4 \times 10^8$ |

TABLE 13

A. niger

| Time Interval | System Evaluated | Dilution | A Plate Count | B Plate Count | Average A&B CFU/ml |
|---|---|---|---|---|---|
| T = 0 day | Test | $10^5$ | 28 | 23 | $2.6 \times 10^6$ |
| | PC | $10^5$ | 20 | 25 | $2.3 \times 10^6$ |
| T = 7 day | Test | $10^3$ | 143 | 91 | $1.2 \times 10^5$ |
| | PC | $10^7$ | 52 | 37 | $4.5 \times 10^8$ |
| T = 14 day | Test | $10^2$ | 47 | 52 | $5 \times 10^3$ |
| | PC | $10^7$ | 31 | 30 | $3.1 \times 10^8$ |
| T = 14 day Rechallenge | Test | $10^3$ | 161 | 149 | $1.5 \times 10^5$ |
| | PCR | $10^4$ | 10 | 12 | $1.1 \times 10^5$ |
| T = 21 day | Test | $10^2$ | 12 | 16 | $1.4 \times 10^3$ |
| | PC | $10^7$ | 47 | 52 | $5 \times 10^8$ |
| | PCR | $10^3$ | 40 | 52 | $4.1 \times 10^4$ |
| T = 28 day | Test | $10^1$ | 27 | 26 | $2.7 \times 10^2$ |
| | PC | $10^7$ | 38 | 54 | $4.6 \times 10^8$ |
| | PCR | $10^3$ | 49 | 47 | $4.8 \times 10^4$ |

TABLE 14

NEUTRALIZER EFFICACY SCREEN
*B. subtilis*

| Time Interval | System Evaluated | Count A | Count B | Average |
|---|---|---|---|---|
| Day = 0 | Test | 60 | 54 | 57 |
| | PC | 51 | 68 | 60 |
| Day = 7 | Test | 92 | 104 | 98 |
| | PC | 91 | 98 | 95 |
| Day = 14 | Test | 25 | 25 | 25 |
| | PC | 14 | 16 | 15 |
| Day = 21 | Test | 14 | 21 | 18 |
| | PC | 21 | 21 | 21 |
| Day = 28 | Test | 51 | 50 | 51 |
| | PC | 45 | 38 | 42 |

EXAMPLE 2

A preservative effectiveness study was conducted using an aqueous solution of 0.1% by weight high purity benzyl alcohol (<100 ppm benzaldehyde), 0.5% trisodium edetate and 2.0% propylene glycol (the formula of Table 1 without Miranol 2 MCA Modified and Triton X-100).

The test system and preparation of the challenge organisms was the same as for Example 1 and the testing procedure was the same as Example 1 except that no rechallenge was performed.

The results of this study are presented in Table 5.

The concentration of *S. aureus, P. aeruginosa* and *E. coli* were reduced to at least 0.1% (three log values) of the initial concentration within the first fourteen (14) days. (Note: The initial concentration may be based upon the Positive Control T=0 Day concentration as a result of cidal action reducing the test sample T=0 Day concentration.) The concentration of viable *C. albicans* and *A. niger* remained at or below the initial concentration during the first fourteen (14) days.

The concentration of the positive controls were not reduced more than 10.0% (one log value).

Solution B as tested with *S. aureus, P. aeruginosa, E. coli, C. albicans* and *A. niger* meets the requirements of Preservative Efficacy after 14 days.

TABLE 15

Solution B

| Organism | E. Coli ATCC 8739 | P. Aeruginosa ATCC 9027 | S. Aureus ATCC 6538 | A. Niger ATCC 16404 | C. Albicans ATCC 10231 |
|---|---|---|---|---|---|
| T = 0 | $1.7 \times 10^6$ | $9.8 \times 10^5$ | $3.1 \times 10^6$ | $5.0 \times 10^{3*}$ | $3.5 \times 10^5$ |
| Positive Control | $2. \times 10^6$ | $1.6 \times 10^6$ | $3.1 \times 10^6$ | $1.1 \times 10^5$ | $2.8 \times 10^5$ |
| T = 7 Days | <10 | $4.10^1$ | <10 | $2.5 \times 10^4$ | $7.8 \times 10^4$ |
| Positive Control | $2.1 \times 10^8$ | $1.5 \times 10^8$ | $2.1 \times 10^8$ | $4.5 \times 10^4$ | $1.3 \times 10^5$ |
| T = 14 Days | <10 | <10 | <10 | $2.8 \times 10^3$ | $9.2 \times 10^4$ |
| Positive Control | $4.1 \times 10^8$ | $1.0 \times 10^9$ | $4.2 \times 10^8$ | $1.2 \times 10^5$ | $4.4 \times 10^5$ |

*Note: For Test No. 1102, T = 0 *A. Niger* plates $10^2$ had approximately 50 colonies also clumped, difficult to enumerate. An initial level comparable to positive control was assumed.

The disclosures of U.S. Pat. Nos. 4,626,292, 4,543,200, 4,560,491 and 4,529,535 are hereby incorporated by reference.

Whereas the present invention has been described with respect to specific embodiments thereof, it will be understood that various changes and modifications will be suggested to one skilled in the art and it is intended that the invention encompass such changes and modifications as fall within the scope of the appended claims.

I claim:

1. A sterile aqueous contact lens wetting solution comprising:
    (i) water and at least one wetting agent for contact lenses, present in an effective amount for wetting;
    (ii) a preservative consisting of effective amounts of high purity benzyl alcohol having a benzaldehyde concentration of less than 100 ppm by weight of benzyl alcohol and a water soluble salt of ethylenediaminetetraacetic acid for maintaining the sterility of said wetting solution; and
    (iii) less than about one ppm by weight benzaldehyde by total weight of said wetting solution.

2. The solution of claim 1 wherein said wetting agent is selected from the group consisting of polyvinyl alcohol, polyvinylpyrrolidone and mixtures thereof.

3. The solution of claim 1 wherein said water soluble salt of ethylenediaminetetraacetic acid of said cleaning and storing solution is trisodiumethylenediaminetetraacetic acid.

4. The solution of claim 1 further comprising an antioxidant for said benzyl alcohol.

5. The solution of claim 4 wherein said antioxidant is a compound of Vitamin A.

6. The solution of claim 2 wherein said wetting agent is polyvinylpyrrolidone and polyvinyl alcohol.

7. A sterile aqueous contact lens wetting solution comprising:
    (i) water and at least one wetting agent for contact lenses, present in an effective amount for wetting and including from about 0.5% to about 2.5% polyvinyl alcohol and from about 0.5% to about 2.0% polyvinylpyrrolidone;
    (ii) a preservative consisting of high purity benzyl alcohol having a benzaldehyde concentration of less than about 100 ppm by weight of benzyl alcohol, the benzyl alcohol being present in an amount of from about 0.005% to about 1.0% benzyl alcohol by weight of the total wetting solution and a water soluble salt of EDTA present in an amount of from about 0.025% to about 0.5% by weight of the total wetting solution and from about 0.001% to about 0.20% sorbic acid by weight of the total wetting solution, for maintaining the sterility of the wetting solution; and
    (iii) less than about one ppm by weight benzaldehyde by total weight of said wetting solution.

8. A sterile aqueous contact lens wetting solution comprising:
    (i) water and at least one wetting agent for contact lenses, present in an effective amount for wetting and including from about 0.5% to about 2.5% polyvinyl alcohol and from about 0.5% to about 2.0% polyvinylpyrrolidone, by weight of the total wetting solution;

(ii) a preservative consisting of from about 0.05% to about 1.0% high purity benzyl alcohol having a benzaldehyde concentration of less than 100 ppm by weight of benzyl alcohol and from about 0.025% to about 0.5% trisodium edetate and from about 0.001% to about 0.20% sorbic acid, for maintaining the sterility of the wetting solution; and (iii) less than about one ppm by weight benzaldehyde by total wight of the wetting solution.

9. The solution of claim 7 wherein said wetting solution further comprises, by weight of the total wetting solution, about 0.138% sodium carbonate, about 0.005% sodium phosphate, about 0.005% sodium biphosphate, about 0.748% sodium chloride, about 0.0280% potassium chloride, about 0.35% hydroxyethylcellulose and about 0.02% sodium bisulfite.

10. A method of wetting a rigid gas permeable contact lens comprising wetting the rigid gas permeable contact lens with an aqueous wetting solution that comprises a hydrophilic preservative system present in an effective amount for maintaining the sterility of said aqueous wetting solution and at least one wetting agent, present in an effective amount for wetting the lens, said preservative system consisting of high purity benzyl alcohol having a benzaldehyde concentration of less than 100 ppm by weight of benzyl alcohol and a water soluble salt of ethylenediaminetetraacetic acid and said aqueous wetting solution containing less than about one ppm benzaldehyde by weight of the wetting solution.

11. The method of claim 10 wherein said wetting agent is selected from the group consisting of polyvinyl alcohol and polyvinylpyrrolidone.

12. The method of claim 10 wherein said water soluble salt of ethylenediaminetetraacetic acid of said cleaning solution is trisodiumethylenediaminetetraacetic acid.

13. The method of claim 10 wherein said wetting agent is polyvinylpyrrolidone and polyvinyl alcohol.

14. The method of claim 10 wherein said aqueous wetting solution comprises, by weight of the total wetting solution:
from about 0.5% to about 2.5% polyvinyl alcohol;
from about 0.5% to about 2.0% polyvinylpyrrolidone;
from about 0.05% to about 1.0% benzyl alcohol; and
from about 0.025% to about 0.5% trisodiumedetate.

15. The method of claim 10 wherein said aqueous wetting solution comprises, by weight of the total wetting solution:
from about 0.5% to about 2.5polyvinyl alcohol;
from about 0.5% to about 2.0% polyvinylpyrrolidone;
from about 0.05% to about 1.0% benzyl alcohol; and
from about 0.025% to about 0.5% of a water soluble salt of EDTA.

16. The method of claim 14 wherein said wetting solution further comprises, by weight of the total wetting solution, about 0.138% sodium carbonate, about 0.005% sodium phosphate, about 0.005% sodium biphosphate, about 0.748% sodium chloride, about 0.280% potassium chloride, about 0.35% hydroxyethylcellulose and about 0.02% sodium bisulfite.

17. A method of cleaning a rigid gas permeable contact lens comprising:
cleaning the rigid gas permeable contact lens with a nonabrasive sterile aqueous cleaning and storing solution that comprises an effective amount of a hydrophilic preservative system consisting of benzyl alcohol and a water soluble salt of ethylenediaminetetraacetic acid for preserving the sterility of said solution, an alkylarylpolyether alcohol nonionic detergent and an amphoteric surface active agent, said alkylarylpolyether alcohol and said surface active agent present in effective amounts for cleaning the rigid gas permeable contact lens.

18. The method of claim 17 wherein said water soluble salt of ethylenediaminetetraacetic acid of said cleaning, and storing solution is trisodiumethylenediaminetetraacetic acid.

19. The method of claim 17 wherein said alkylarylpolyether alcohol non-ionic detergent is an isooctylphenoxypolyethoxyethanol.

20. The method of claim 17 wherein said amphoteric surface active agent is 2-cocyl-2-imidazolinium lauryl sulfate-1-carboxymethyloxyethyl-1-carboxymethyl disodium.

21. The method of claim 17 wherein said solution has a pH in the range of from about 6.5 to 8.5 and a tonicity in the range of from about 0.91 to 1.65.

22. The method of claim 17 wherein said solution comprises, by weight of the total composition:
from about 0.5% to about 20% 2-cocyl-2-imidazolinium lauryl sulfate-1-carboxymethyloxyethyl-1-carboxymethyl disodium;
from about 0.005% to about 5.0% isooctylphenoxypolyethoxyethane;
from about 0.05% to about 1.0% benzyl alcohol; and
from about 0.025% to about 0.5% trisodiumedetate.

23. The method of claim 22 wherein said solution further comprises from about 0.005% to about 5.0% propylene glycol by weight of the total composition.

24. The method of claim 17 further comprising storing said lens in said cleaning and storing solution after said cleaning step.

25. The method of claim 24 wherein said storing helps to remove contaminants remaining after said cleaning.

26. A sterile aqueous cleaning and storing solution for rigid gas permeable lenses comprising: water; a preservative component consisting of effective amounts of benzyl alcohol and a water soluble salt of EDTA, for maintaining the sterility of the cleaning and storing solution; an alkylarylpolyether alcohol non-ionic detergent and an amphoteric surface active agent, present in effective amounts for cleaning the rigid gas permeable contact lens to allow wetting by a wetting solution; and less than about one ppm of benzaldehyde by total weight of the solution.

27. A sterile aqueous wetting solution for rigid gas permeable contact lenses comprising:
(a) at least one wetting agent for rigid gas permeable lenses, present in an effective amount for wetting a rigid gas permeable contact lens; and
(b) a preservative system consisting of high purity benzyl alcohol having a benzaldehyde concentration of less than 100 ppm by weight of benzyl alcohol and a water soluble salt of ethylenediaminetetraacetic acid, present together in effective amounts in said wetting solution for maintaining the sterility of said wetting solution; and
(c) less than about one ppm benzaldehyde by weight of the total solution.

28. A contact lens preservative composition for maintaining the sterility of a sterile solution for contact lenses, consisting of high purity benzyl alcohol having a benzaldehyde concentration of less than 100 ppm by weight of benzyl alcohol and a water soluble salt of ethylenediaminetetraacetic acid.

29. An aqueous sterile contact lens solution comprising:
water;
optionally at least one component selected from the group consisting of wetting agents, cleaning agents, salts;
a preservative system consisting of high purity benzyl alcohol having a benzaldehyde concentration of less than 100 ppm by weight of benzyl alcohol in an amount sufficient to preserve the sterility of the solution; and
less than about one ppm benzaldehyde by weight of the total solution.

30. The solution of claim 29 wherein said high purity benzyl alcohol is present in an amount of from about 0.05% to about 1.0% by weight of the total solution.

31. The solution of claim 29 wherein said high purity benzyl alcohol is present in an amount of about 0.1% by weight of the solution.

32. An aqueous sterile contact lens solution comprising:
water;
optionally at least one component selected from the group consisting of wetting agents, cleaning agents, salts;
a preservative system consisting of high purity benzyl alcohol having a benzaldehyde concentration of less than 100 ppm by weight of benzyl alcohol and a water soluble salt of ethylenediaminetetraacetic acid in an amount sufficient to preserve the sterility of the solution; and
less than about 1 ppm benzaldehyde by weight of the total solution.

33. The solution of claim 29 wherein said contact lens solution is a wetting solution containing at least one wetting agent.

34. The solution of claim 29 wherein said contact lens solution is a cleaning solution containing at least one cleaning agent.

35. The solution of claim 29 wherein said contact lens solution is a storing solution.

36. The solution of claim 29 wherein said solution is an in-eye rewetting solution.

37. The solution of claim 29 wherein said solution is a saline solution.

38. An aqueous sterile contact lens cleaning and storage solution comprising:
water;
an amphoteric surface active agent present in an amount of about 8%, an alkylarylpolyether alcohol present in an amount of about 2.33%, all by weight of the total aqueous composition;
a preservative system consisting of high purity benzyl alcohol present in an amount of about 0.1%, trisodium edetate present in an amount of about 0.5%, all by weight of the total aqueous composition;
propylene glycol present in an amount of about 2.0% by weight of the total aqueous composition; and
less than about one ppm benzaldehyde by weight of the total aqueous composition.

39. An aqueous sterile contact lens solution comprising:
water;
optionally at least one component selected from the group consisting of wetting agents, cleaning agents, salts;
a preservative comprising high purity benzyl alcohol having a benzaldehyde concentration of less than 100 ppm by weight of benzyl alcohol in an amount sufficient to preserve the sterility of the solution;
less than about one ppm benzaldehyde by weight of the total solution; and
wherein said solution is a wetting and in-eye comfort drop comprising about 0.1% benzyl alcohol, about 0.1% of a Vitamin A emulsifier, about 0.0196% Vitamin A Palmitate, about 0.5% polyvinylpyrrolidone, about 1.0% polyvinyl alcohol, about 0.27% hydroxyethylcellulose and about 0.1% trisodium edetate, all be weight of the total aqueous composition.

40. A contact lens preservative system for maintaining the sterility of a sterile solution for contact lenses, comprising high purity benzyl alcohol having a benzaldehyde concentration of less than 100 ppm of benzyl alcohol, a water soluble salt of ethylenediaminetetraacetic acid, an antioxidant for said benzyl alcohol wherein said antioxidant is a Vitamin A compound.

41. A contact lens preservative system for maintaining the sterility of a sterile solution for contact lenses comprising high purity benzyl alcohol having a benzaldehyde concentration of less than 100 ppm of benzyl alcohol, a water soluble salt of ethylenediaminetetraacetic acid, an antioxidant for said benzyl alcohol wherein said antioxidant is Vitamin A Palmitate.

42. An aqueous sterile contact lens solution comprising:
water;
optionally at least one component selected from the group consisting of wetting agents, cleaning agents, salts;
a preservative comprising high purity benzyl alcohol having a benzaldehyde concentration of less than a 100 ppm by weight of benzyl alcohol in an amount sufficient to preserve the sterility of the solution;
less than about one ppm benzaldehyde by weight of the total solution; and
an antioxidant for said benzyl alcohol wherein said antioxidant is a Vitamin A compound.

43. An aqueous sterile contact lens solution comprising:
water;
optionally at least one component selected from the group consisting of wetting agents, cleaning agents, salts;
a preservative comprising high purity benzyl alcohol having a benzaldehyde concentration of less than 100 ppm by weight of benzyl alcohol in an amount sufficient to preserve the sterility of the solution;
less than about one ppm benzaldehyde by weight of the total solution; and
an antioxidant for said benzyl alcohol wherein said antioxidant is a Vitamin A Palmitate.

44. A cleaning, storing and wetting solution system for rigid, gas permeable lenses comprising a nonabrasive sterile aqueous cleaning and storing solution and a separate sterile aqueous wetting solution,
(a) said sterile aqueous cleaning and storing solution for rigid gas permeable lenses comprising:
(i) a preservative system consisting of effective amounts of benzyl alcohol and a water soluble salt of ethylenediaminetetraacetic acid for maintaining the sterility of the cleaning and storing solution;

(ii) an alkylarylpolyether alcohol non-ionic detergent and an amphoteric surface active agent, present in effective amounts for cleaning the rigid gas permeable contact lens; and (b) said sterile aqueous wetting solution comprising:

(i) at least one wetting agent for rigid gas permeable lenses, present in an effective amount for wetting; and (ii) a preservative system consisting of effective amounts of high purity benzyl alcohol having a benzaldehyde concentration of less than 100 ppm by weight of benzyl alcohol and a water soluble salt of ethylenediaminetetraacetic acid for maintaining the sterility of said wetting solution.

45. The system of claim 44 wherein said wetting agent is selected from the group consisting of polyvinyl alcohol polyvinylpyrrolidone, and mixtures thereof.

46. The system of claim 44 wherein said water soluble salt of ethylenediaminetetraacetic acid of said cleaning and storing solution is trisodiumethylenediaminetetraacetic acid.

47. The system of claim 44 wherein said alkylarylpolyether alcohol non-ionic detergent is an isooctylphenoxypolyethoxyethanol.

48. The system of claim 44 wherein said amphoteric surface active agent is 2-cocoyl-2-imidazolinium lauryl sulfate-1-carboxymethyloxyethyl-1-carboxymethyl disodium.

49. The system of claim 45 wherein said wetting agent is polyvinylpyrrolidone and polyvinyl alcohol.

50. The system of claim 44 wherein said cleaning and storage solution has a pH in the range of from about 6.5 to 8.5 and a tonicity in the range of from about 0.91 to 1.65.

51. A method of treating and caring for a rigid gas permeable contact lens with first and second nonabrasive aqueous solutions, comprising:

(a) cleaning the rigid gas permeable lens with said first aqueous solution, which solution comprises: a preservative consisting of high purity benzyl alcohol having a benzaldehyde concentration of less than 100 ppm by weight of benzyl alcohol and a water soluble salt of EDTA, present in an effective amount for maintaining the sterility of said first solution, an alkylarylpolyether alcohol nonionic detergent and an amphoteric surface active agent, present in an effective amount for cleaning the rigid gas permeable contact lens; and thereafter (b) wetting the rigid gas permeable contact lens with said second aqueous solution that comprises a preservative system present in an effective amount for maintaining the sterility of said second solution and at least one wetting agent, present in an effective amount for wetting the lens, said preservative system consisting of high purity benzyl alcohol having a benzaldehyde concentration of less than 100 ppm by weight of benzyl alcohol.

52. The method of claim 51 further comprising storing the rigid gas permeable lens between wearing periods after said cleaning step in the cleaning solution to help disperse any contaminants remaining after cleaning.

53. The method of claim 51 wherein said wetting agent is selected from the group consisting of polyvinyl alcohol and polyvinylpyrrolidone.

54. The method of claim 51 wherein said water soluble salt of ethylenediaminetetraacetic acid of said cleaning, conditioning and storing solution is trisodiumethylenediaminetetraacetic acid.

55. The method of claim 51 wherein said alkylarylpolyether alcohol non-ionic detergent is an isooctylphenoxypolyethoxyethanol.

56. The method of claim 51 wherein said amphoteric surface active agent is 2-cocyl-2-imidazolinium lauryl sulfate-1-carboxymethyloxyethyl-1-carboxymethyl disodium.

57. The method of claim 51 wherein said wetting agent is polyvinylpyrrolidone and polyvinyl alcohol.

58. The method of claim 51 wherein said cleaning, conditioning and storage solution has a pH in the range of from about 6.5 to 8.5 and a tonicity in the range of from about 0.91 to 1.65.

59. An aqueous sterile contact lens solution comprising:

water;

wetting agents including about 1.0% polyvinyl alcohol, about 0.5% polyvinylpyrrolidone and about 0.35% hydroxyethylcellulose, all by weight of the total aqueous composition;

a preservative system consisting of about 0.1% high purity benzyl alcohol by weight of the total aqueous composition, said high purity benzyl alcohol having a benzaldehyde concentration of less than 100 ppm by weight of benzyl alcohol and about 0.1% trisodium edetate by weight of the total aqueous composition.

* * * * *